United States Patent
Olmstead

(10) Patent No.: US 11,078,516 B2
(45) Date of Patent: Aug. 3, 2021

(54) INHIBITION AND TREATMENT OF GASTROINTESTINAL BIOFILMS

(71) Applicant: Prothera, Inc., Reno, NV (US)

(72) Inventor: Stephen Francis Olmstead, Reno, NV (US)

(73) Assignee: Prothera, Inc., Reno, NV (US)

(*) Notice: Subject to any disclaimer, the term of this patent is extended or adjusted under 35 U.S.C. 154(b) by 0 days.

(21) Appl. No.: 15/979,362

(22) Filed: May 14, 2018

(65) Prior Publication Data

US 2018/0258460 A1     Sep. 13, 2018

Related U.S. Application Data

(63) Continuation of application No. 12/368,259, filed on Feb. 9, 2009, now abandoned.

(60) Provisional application No. 61/065,186, filed on Feb. 8, 2008.

(51) Int. Cl.

| | |
|---|---|
| *A61K 38/47* | (2006.01) |
| *A61K 38/48* | (2006.01) |
| *A61P 43/00* | (2006.01) |
| *A61P 31/04* | (2006.01) |
| *C12Q 1/18* | (2006.01) |
| *A61K 31/70* | (2006.01) |
| *A61K 38/46* | (2006.01) |

(52) U.S. Cl.
CPC .......... *C12Q 1/18* (2013.01); *A61K 31/70* (2013.01); *A61K 38/465* (2013.01); *A61K 38/47* (2013.01); *A61K 38/48* (2013.01); *G01N 2333/914* (2013.01); *G01N 2500/04* (2013.01)

(58) Field of Classification Search
CPC ......... A61K 38/47; A61K 38/48; A61P 43/00; A61P 31/00; A61P 31/04; G01N 2333/914

See application file for complete search history.

(56) References Cited

U.S. PATENT DOCUMENTS

| | | | |
|---|---|---|---|
| 4,994,390 A | 2/1991 | Wiatr | |
| 5,324,514 A | 6/1994 | Sipos | |
| 5,445,957 A | 8/1995 | Rohde, Jr. et al. | |
| 5,510,104 A | 4/1996 | Allen | |
| 5,624,678 A | 4/1997 | Bedford et al. | |
| 6,100,080 A * | 8/2000 | Johansen | A61L 2/186 |
| | | | 435/264 |
| 6,365,208 B1 | 4/2002 | Kulkarni et al. | |
| 6,558,693 B1 | 5/2003 | Knap et al. | |
| 6,562,340 B1 | 5/2003 | Bedford et al. | |
| 6,699,496 B1 | 3/2004 | Kojima et al. | |
| 6,756,489 B1 | 6/2004 | Schmidt et al. | |
| 6,759,040 B1 * | 7/2004 | Manyak | A61L 2/186 |
| | | | 424/94.2 |
| 6,780,628 B2 | 8/2004 | Anderson et al. | |
| 6,855,548 B2 | 2/2005 | Sjoeholm et al. | |
| 6,900,173 B2 | 5/2005 | Martin et al. | |
| 7,011,964 B2 | 3/2006 | Bedford et al. | |
| 7,041,470 B2 | 5/2006 | Ceri et al. | |
| 7,060,674 B2 | 6/2006 | Lim et al. | |
| 7,067,124 B2 | 6/2006 | Davidson et al. | |
| 7,153,503 B1 | 12/2006 | Henderson | |
| 7,217,433 B2 | 5/2007 | Hansen et al. | |
| 7,220,404 B2 | 5/2007 | Morgan et al. | |
| 7,229,809 B2 | 6/2007 | Veronesi et al. | |
| 7,235,390 B2 | 6/2007 | Gibbs | |
| 7,307,062 B2 | 12/2007 | Bolte | |
| 8,383,101 B2 | 2/2013 | Olmstead | |
| 8,728,467 B2 | 5/2014 | Olmstead | |
| 2002/0003726 A1 | 3/2002 | Budny et al. | |
| 2002/0037260 A1 * | 3/2002 | Budny | A61K 8/64 |
| | | | 424/49 |
| 2002/0187953 A1 | 12/2002 | Aubin et al. | |
| 2003/0113742 A1 | 6/2003 | Whiteley et al. | |
| 2003/0215433 A1 | 11/2003 | Kokai-Kun et al. | |
| 2004/0005304 A1 | 1/2004 | Brudnak | |
| 2004/0062757 A1 | 4/2004 | Finegold | |

(Continued)

FOREIGN PATENT DOCUMENTS

| | | |
|---|---|---|
| DE | 102005049649 A1 | 4/2007 |
| WO | 9631610 A2 | 10/1996 |

(Continued)

OTHER PUBLICATIONS

Swidsinski et al. Bacterial Biofilm Within Diseased Pancreatic and Biliary Tracts; Gut, vol. 54, pp. 388-395. (Year: 2005).*
Serva Electrophoresis. Cellulases, pp. 1-2. downloaded from: http://www.serva.de/www_root/documents/16419+26.pdf on Mar. 11, 2019. (Year: 2020).*
Selan et al. Proteolytic Enzymes: A New Treatment Strategy for Prosthetic Infections?; Antimicrobial Agents and Chemotherapy, vol. 37, No. 12, pp. 2618-2621. (Year: 1993).*

(Continued)

*Primary Examiner* — Susan M Hanley
*Assistant Examiner* — Paul C Martin
(74) *Attorney, Agent, or Firm* — McBee Moore & Vanik IP, LLC

(57) ABSTRACT

Orally administered physiologically acceptable anti-biofilm compositions comprising enzymes and if desired additional components such as antimicrobials, antibiotics, antifungals, herbals, chelating agents, lactoferrin and related compounds, minerals, surfactants, binders, and fillers useful for the inhibition and treatment of gastrointestinal biofilms in humans. Physiologically acceptable anti-biofilm compositions containing these enzymes are useful in the inhibition, reduction and/or treatment of gastrointestinal biofilm infections, and associated systemic symptoms caused by biofilms associated microorganisms within the gastrointestinal tract. Methods of identification, preparation and use of such physiologically acceptable anti-biofilm compositions are also provided.

3 Claims, No Drawings

(56) References Cited

U.S. PATENT DOCUMENTS

| | | | |
|---|---|---|---|
| 2004/0109852 A1 | 6/2004 | Xu | |
| 2004/0170617 A1 | 9/2004 | Finegold | |
| 2004/0247618 A1 | 12/2004 | Gibbs | |
| 2005/0003503 A1 | 1/2005 | Manyak et al. | |
| 2005/0058744 A1 | 3/2005 | Steinberg et al. | |
| 2005/0079594 A1 | 4/2005 | Marion et al. | |
| 2005/0112200 A1 | 5/2005 | Grossman et al. | |
| 2005/0158253 A1 | 7/2005 | Budny et al. | |
| 2006/0083727 A1 | 4/2006 | Kajander et al. | |
| 2006/0111299 A1 | 5/2006 | Kisilevsky et al. | |
| 2006/0115436 A1 | 6/2006 | Haberlein et al. | |
| 2006/0134018 A1 | 6/2006 | Trivedi et al. | |
| 2006/0140881 A1* | 6/2006 | Xu | A61K 8/498 424/49 |
| 2006/0177424 A1 | 8/2006 | Cobb et al. | |
| 2006/0182802 A1 | 8/2006 | Shimizu et al. | |
| 2006/0211049 A1 | 9/2006 | Aubin et al. | |
| 2006/0246049 A1 | 11/2006 | Kaplan | |
| 2006/0272102 A1 | 12/2006 | Liu et al. | |
| 2007/0020237 A1 | 1/2007 | Yoon et al. | |
| 2007/0116698 A1 | 5/2007 | Perraudin | |
| 2007/0244059 A1 | 10/2007 | Karaolis | |
| 2007/0258913 A1 | 11/2007 | Rossel | |
| 2007/0280910 A1 | 12/2007 | Cobb et al. | |
| 2007/0280911 A1 | 12/2007 | Cobb et al. | |
| 2007/0280912 A1 | 12/2007 | Cobb et al. | |
| 2009/0162301 A1* | 6/2009 | Tarrand | A01N 59/12 424/51 |

FOREIGN PATENT DOCUMENTS

| | | | |
|---|---|---|---|
| WO | 0141785 A2 | 6/2001 | |
| WO | 0149128 A1 | 7/2001 | |
| WO | 0193904 A1 | 12/2001 | |
| WO | 03082148 A1 | 10/2003 | |
| WO | 2004/066945 A2 | 8/2004 | |
| WO | 2004066945 A2 | 8/2004 | |
| WO | 2008035371 A2 | 3/2008 | |

OTHER PUBLICATIONS

Glade et al. Improvement in Protein Utilization in Nursing-Home Patients On Tube Feeding Supplemented With an Enzyme Product Derived From Aspergillus Niger and Bromelain; Nutrition, vol. 17, No. 4, pp. 348-350. (Year: 2001).*

Anonymous. AbsorbAid Digestive Support. Downloaded from http://www.us.fullscript.com/products/absorbaid-digestive-support-240-vcaps on Mar. 11, 2020. (Year: 2020).*

Shimosaka et al. Production of Two Chitosanases From a Chitosan-Assimilating Bacterium, *Acinetobacter* sp. Strain CHB101; Applied and Environmental Microbiology, vol. 61, No. 2, pp. 438-442. (Year: 1995).*

Whitchurch et al. Extracellular DNA Required for Bacterial Biofilm Formation; Science, vol. 295, p. 1487. (Year: 2002).*

Anonymous. Undecylenic Acid; Alternative Medicine Review, vol. 7, No. 1 pp. 68-70. (Year: 2002).*

Lambier et al. Dipeptidyl-Peptidase IV From Bench To Bedside: An Update On Structural Properties, Functions, and Clinical Aspects of teh Enzyme DPP IV; Critical Reviews in Clinical Laboratory Sciences, vol. 40, No. 3, pp. 209-294. (Year: 2003).*

Urbanek et al. Isolation and Properties of Extracellular Cellulase-Hemicellulase Complex of Phoma Hibernica; Archives of Microbiology, vol. 118, pp. 265-269. (Year: 1978).*

Parsek, Matthew R., et al. "Bacterial Biofilms: An Emerging Link to Disease Pathogenesis," Annu. Rev. Microbiol., (2003), vol. 57: 677-701.

Coticchia, James M., et al. "Presence and Density of Helicobacter pylori Biofilms in Human Gastric Mucosa in Patients with Peptic Ulcer Disease," Journal of Gastrointestinal Surgery, (2006), vol. 10, No. 6: 883-889.

Potera, Carol. "Forging a Link Between Biofilms and Disease," Science, (1999), vol. 283: 1837-1839.

Loiselle, Melanie, et al. "The Use of Cellulase in Inhibiting Biofilm Formation from Organisms Commonly Found on Medical Implants," Biofouling, (2003), vol. 19, No. 2: 77-85.

Donlan, Rodney M., "Biofilms and Device-Associated Infections," Emerging Infectious Diseases, (2001), vol. 7, No. 2:277-281.

Donlan, Rodney M., el al., "Biofilms: Survival Mechanisms of Clinically Relevant Microorganisms," Clinical Microbiology Reviews, (2002), vol. 15, No. 2: 167-193.

Donskey, Curtis J., "The Role of the Intestinal Tract as a Reservoir and Source for Transmission of Nosocomial Pathogens," Healthcare Epidemiology, (2004), vol. 39: 219-226.

Itoh, Yoshikane, et al., "Depolymerization of beta-1,6-N-Acetyl-D-Glucosamine Disrupts the Integrity of Diverse Bacterial Biofilms," Journal of Bacteriology, (2005), vol. 187, No. 7: 382-387.

Joshua, G. W. P., et al., "Biofilm formation in Campylobacter jejuni," Microbiology, (2006), vol. 152: 387-396.

Kaplan, Jeffrey B., et al, "Detachment of Actinobacillus actinomycelemcomitans Biofilm Cells by an Endogenous beta-Hexosaminidase Activity," Journal of Bacteriology, (2003), vol. 185, No. 16: 4693-4698.

Knutton, Stuart, et al., "In Vitro Adhesion of Enterotoxigenic *Escherichia coli* to Human Intestinal Epithelial Cells from Mucosal Biopsies," Infection and Immunity, (1984), vol. 44, No. 2: 514-518.

Ledeboer, Nathan A., et al., "Exopolysaccharide Sugars Contribute to Biofilm Formation by *Salmonella enterica* Serovar Typhimurium on HEp-2 Cells and Chicken Intestinal Epithelium," Journal of Bacteriology, (2005), vol. 187, No. 9: 3214-3226.

Lee, Keehoon, et al., "Phenotypic and functional characterization of Bacillus anthracis biofilms," Microbiology, (2007), vol. 153: 1693-1701.

Macfarlane, Sandra, et al., "Composition and Metabolic Activities of Bacterial Biofilms Colonizing Food Residues in the Human Gut," Applied and Environmental Microbiology, (2006), vol. 72, No. 9: 6204-6211.

Nivens, David E., et al., "Role of Alginate and Its O Acetylation in Formation of Pseudomonas aeruginosa Microcolonies and Biofilms," Journal of Bacteriology, (2001), vol. 183, No. 3: 1047-1057.

Probert, H.M. et al., "Bacterial Biofilms in the Human Gastrointestinal Tract," Curr. Issues Intest. Microbiol. (2002), vol. 3: 23-27.

Prouty, A. M., et al., "Biofilm Formation and Interaction with the Surfaces of Gallstones by *Salmonella* spp." Infection and Immunity, (2002), vol. 70, No. 5: 2640-2649.

Roberfroid, Marcel. "Prebiotics: The Concept Revisited1,2," The Journal of Nutrition, (2007), vol. 137: 830S-837S.

Rouquette, Corinne, et al., "The pathogenesis of infection by Listeria monocytogenes," Microbiologia SEM, (1996), vol. 12: 245-258.

Styer, Katie L., et al., "Yersinia pestis kills Caenorhabditis elegans by a biofilm-independent process that involves novel virulence factors," EMBO Reports, (2005), vol. 6, No. 10: 992-997.

Tan, Li, et al., "A Movable Surface: Formation of *Yersinia* sp. Biofilms on Motile Caenorhabditis elegans," Journal of Bacteriology, (2004), vol. 186, No. 15: 5087-5092.

Wikipedia.com, "Biofilm," https://en.wikipedia.org/wiki/biofilm, accessed Dec. 16, 2019.

Wozniak, Daniel J., et al., "Alginate is not a significant component of the extracellular polysaccharide matrix of PA14 and PA01 Pseudomonas aeruginosa biofilms," Proc. Natl. Mad. Sci., (2003), vol. 100, No. 13: 7907-7912.

Sellman, S. "Serrapeptiase: An Amazing Gift from the Silk Worm," (2003), downloaded from http://www.life-enthusiast.com/enzyme/serrapeptase.pdf on Mar. 25, 2016.

Ikeda, et la. Agr. Biol. chem. (1067) 31(10): 1201-1209.

Kuo et al. Bioresource Technology (2009) 100: 866-871.

Hayworth, D. Dialysis Methods for Protein Research downloaded from http://www.piercenet.com/method/dialysis-methods-protein-research Oct. 3, 2014.

International Search Report dated Sep. 10, 2009, for International Application No. PCT/US2008/033599 filed Feb. 9, 2009.

Written Opinion dated Sep. 10, 2009, for International Application No. PCT/US2009/033599 filed Feb. 9, 2009.

Rossi, et al. (1983), "Senratio-Peptidase in the Treatment of Serious Otitis Media in Children," Otorinolaringologia: 33(2): 169-174.

(56) References Cited

OTHER PUBLICATIONS

Orgaz et al. Eng. Microb. Tchnol. (2006) 40: 51-56.
Moriya et al. Biotechnol. Appl. Biochem. (1994) 20: 101-108.
Definition of Serrapeptase from emedicinehealth website: www.emedicinehealth.com/serrapeptase/vitamins-supplements.htm downloaded Apr. 4, 2012; 2 pages.
Taber's Cyclopedic Medical Dictionary. Clayton Thomas, Ed. 15th edition. (F.A. Davis: Philadelphia, PA) (1985) pp. 102-103.
Trampuz et al. Swiss Medical Weekly (2005) 135(17-18): 243-251.
British Universities Film & Video Council website http://bufvc.ac.uk/dvdfind/index.php/title/20301 downloaded Apr. 6, 2012: 1 page.
Machine translation of DE 102005049649 downloaded from the EPO Apr. 2, 2012.
Novak et al. J. Am. Oil Chem. Soc. (1961) 38: 321-4.

\* cited by examiner

INHIBITION AND TREATMENT OF GASTROINTESTINAL BIOFILMS

This application is a divisional of U.S. application Ser. No. 12/368,259 filed Feb. 9, 2009 (now abandoned); the entire contents of which are incorporated by reference. The present application also claims the benefit of U.S. Provisional Patent Application Ser. No. 61/065,186 filed Feb. 8, 2008, which application is incorporated herein by reference in its entirety.

BACKGROUND

A "biofilm" is a well known phenomenon and may be defined as a population of prokaryotic cells growing on a surface and enclosed in a self-produced matrix of extracellular polymeric material, which mediates adhesion of the cells to each other and to surfaces. Biofilms are not simply passive assemblages of cells that are stuck to surfaces, but are structurally and dynamically complex biological systems. As compared with cells that are planktonic in nature, bacteria growing in biofilms exhibit a different phenotype with respect to growth rate and gene transcription. See en.wikipedia.org/wiki/Biofilm.

Unwanted biofilms have been responsible, for example, for the fouling of cooling-water towers, water pipelines, membrane units and food-processing plants. Biofilms are notoriously difficult to eradicate. Microbes in industrial biofilms are protected from antimicrobial chemicals, environmental bacteriophages, and phagocytic amoebae. (Donlan R M, Costerton J W. Biofilms: survival mechanisms of clinically relevant microorganisms. Clin Microbiol Rev 2002; 15167-293.)

In addition to their importance in industry, biofilms may be involved in a significant percentage of human microbial infections (Potera C. Forging a link between biofilms and disease. Science 1999; 283:1837-8). Parsek and Singh proposed four criteria for defining a biofilm etiology of an infection: the pathogenic bacteria are surface associated or adherent to a substratum; direct examination reveals bacteria in clusters, encased in a matrix of bacterial or host constituents; the infection is localized; and the infection is resistant to antibiotic therapy despite the antibiotic sensitivity of the constituent planktonic organisms (Parsek M R, Singh P K. Bacterial biofilms: an emerging link to disease pathogenesis. Annu Rev Microbiol 2003; 57:677-701.)

Biofilm infections can be involved in the etiology of dental caries, periodontal disease, cystic fibrosis (CF) airway infections, native valve endocarditis, chronic bacterial prostatitis, otitis media, and vaginal infections. Biofilm microorganisms are also involved in implant-related infections, in which adherent microbial populations form on the surfaces of catheters, prosthetic heart valves, joint replacements, and other devices (Donlan R M. Biofilms and device-associated infections. Emerg Infect Dis 2001; 7:277-81.)

The intestinal tract provides a reservoir for many antibiotic-resistant biofilm bacteria, including *Enterobacteriaceae* species, *Pseudomonas aeruginosa*, and *Acinetobacter* species (Donskey C J. The role of the intestinal tract as a reservoir and source for transmission of nosocomial pathogens. Clin Infect Dis 2004; 39:219-26.) The human opportunistic pathogen, *Pseudomonas aeruginosa*, is a major cause of infection-related mortality among the critically ill patients, and carries one of the highest case fatality rates of all gram-negative infections. Although the lungs have been traditionally considered to be a major site of *P. aeruginosa* infection among critically ill patients, a significant number of these infections arise as a result of direct contamination of the airways by the gastrointestinal flora or by hematogenous dissemination from the intestines to the lung parenchyma. Effective methods for the inhibition, reduction and/or treatment of *P. aeruginosa* would have a significant impact for this condition.

With respect to biofilms in the gut, it is now known that bacteria can exist for example as biofilms on the colonic epithelium, within the mucus layer covering it, and on food particles in the lumen. (MacFarlane S, MacFarlane G T. Composition and metabolic activities of bacterial biofilms colonizing food residues in the gastrointestinal tract. Appl Environ Microbiol 2006; 72:6204-11; Probert H M, Gibson G R. Bacterial biofilms in the human gastrointestinal tract. Curr Issues Intest Microbiol 2002; 3:23-7.)

Gastrointestinal biofilm-associated bacteria include *Bacteroides* ssp., *Clostridium* ssp., *Fusobacterium* ssp., *Klebsiella* ssp., *Spirochaetes* ssp., *Pseudomonas aeriginosa, Escherichia coli, Helicobacter pylori, Bifidobacterium* ssp., and gram-positive cocci.

Thus, there has gone unmet a need for improved methods, compositions, etc., related to reduction of biofilms within the gut of mammals. The present methods, etc., provide these and/or other advantages.

SUMMARY

The present compositions, medicaments, therapeutics, systems, methods, etc., are directed to the reduction of gastrointestinal biofilm(s) in the gut of animals. The methods include screening for physiologically acceptable anti-biofilm compositions, including for example nutraceutical, therapeutic, or pharmaceutical compositions, comprising anti-biofilm enzymes and other components suitable for oral ingestion by mammals such as humans, and methods of making and using or administering such compositions.

In one aspect, the present compositions, methods, etc., are directed to screening digestive enzymes in biofilm models to identify useful enzymes and compositions for the physiologically acceptable anti-biofilm compositions, treatment methods, etc., discussed herein. Such enzymes may be screened as single agents, mixtures of agents, or in combination with antimicrobial agents, chelating agents, lactoferrin, herbals or other components as desired.

In another aspect, the present physiologically acceptable anti-biofilm compositions, methods, etc., are also directed to the use of digestive enzymes for the inhibition and reduction of pathogenic biofilm in the gastrointestinal tract of humans.

For example, the physiologically acceptable anti-biofilm compositions, methods, etc., can be directed to the use of cellulases, hemicellulases, lysozyme, pectinases, amylases, DNase I, *Serratia* peptidase, and other hydrolases that are capable of digesting the exopolysaccharide and exoprotein matrix of biofilms.

The present physiologically acceptable anti-biofilm compositions, methods, etc., are also directed to oral physiologically acceptable anti-biofilm compositions for the inhibition and treatment of pathogenic gastrointestinal biofilms in humans.

In certain embodiments, the present physiologically acceptable anti-biofilm compositions, methods, etc., are directed to agents that are foodborne, waterborne or are nosocomial. Some embodiments are further directed to biofilm infections that are antibiotic-resistant and/or recurrent. The physiologically acceptable anti-biofilm compositions, etc., may be used in conjunction with antibiotics or antimicrobials. In addition these physiologically acceptable anti-biofilm compositions may be used in patients whose biofilm infections have failed to respond to antibiotics or antimicrobials.

The present physiologically acceptable anti-biofilm compositions, methods, etc., are also directed to the inhibition and treatment of biofilm infections caused by bioterrorist agents.

These and other aspects, features, and embodiments are set forth within this application, including the following Detailed Description. Unless expressly stated otherwise, all embodiments, aspects, features, etc., can be mixed and matched, combined, and permuted in any desired manner.

DETAILED DESCRIPTION

Gastrointestinal biofilms in mammals have been implicated in a variety of possible diseases, either as causing such diseases or making them worse. The present compositions, systems, methods, etc., are directed to the reduction of gastrointestinal biofilm(s) in the gut of animals. The methods include inhibiting, treating, or reducing biofilms in the gastrointestinal system.

Screening For Anti-Biofilm Enzymes

Biofilm devices, such as the Calgary Biofilm Device (Ceri et al., 1999; U.S. Pat. No. 7,041,470) can be modified, for example, to be used in conjunction with the present methods, to identify physiologically acceptable anti-biofilm compositions, etc., to screen for enzymes that are (a) orally available; (b) generally recognized as safe (GRAS); (c) are known to or can be established to retain their activity during passage through the stomach; and (d) are active in disrupting biofilms in model systems. Other devices that are suitable for the study of biofilms afflicting humans may be used. As discussed in Ceri, a Calgary Biofilm Device (CBD) provides for rapid and reproducible assay of biofilm susceptibilities to antibiotics using 96 equivalent biofilms in a standard 96-well plate (or other suitable number as desired), which biofilms are then exposed to the antibiotics under investigation. In the present discussion, such screening biofilms are exposed to enzyme concentrations, etc., as discussed herein. Biofilm formation can be, for example, followed by quantitative microbiology and scanning electron microscopy.

Exemplary Enzymes that Treat, Inhibit, Etc., Biofilms

Bacterial growth on a gastrointestinal surface often involves the self-production of a polysaccharide-rich extracellular matrix that provides structural support for the formation of biofilm communities. Enzymes that disrupt the biofilm matrices of these organisms within the gastrointestinal tract are the subject of the methods, etc., herein.

The particular enzyme(s) to be used may be selected according to the properties, if known, of the specific biofilm to be removed, or a combination of several enzymes having different enzyme activities may be used. The composition of the extracellular matrix is complex and variable among different bacterial species and even within the same species under different environmental conditions. Despite their heterogeneous composition, exopolysaccharides are a typical compound of the biofilm matrix, providing the framework into which microbial cells are inserted. Among the many different exopolysaccharides that have been described, cellulose and β-1,6-linked N-acetylglucosamine appear to be the most common components of the biofilm matrix of many different bacteria.

In one aspect the suitable, physiologically acceptable anti-biofilm compositions, etc., herein comprises an amount of anti-polymeric β-1,6-N-acetyl-D-glucosamine (poly-β-1,6-GlcNAc) agents to substantially disperse poly-(β-1,6-GlcNAc and thus capable of significant biofilm degradation. E.g., see Itoh Y, Wang X, Hinnebusch B J, Preston J F, Romeo T. Depolymerization of β-1,6-N-acetyl-D-glucosamine disrupts the integrity of diverse bacterial biofilms. J Bacteriol 2005; 187; 382-7) In some embodiments, for this and other agents, either alone or in combination, such significant reduction means, if measured in vitro, a log reduction of 1, typically 1.5, or 3.0-3.8 or better. In vivo, such significant reduction can be substantial reduction of one or more symptoms associated with a biofilm infection, or even substantial elimination of one or more symptoms associated with a biofilm infection. Exemplary anti-GlcNAc-agents include a previously identified .uparw.-hexosaminidase and biofilm-dispersing enzyme of A. actinomycetemcomitans, DspB or dispersin B, which specifically hydrolyzes the glycosidic linkages of poly-β-1,6-GlcNAc and disrupts bacterial biofilm (Kaplan J B, Ragunath C, Ramasubbu N, Fine D H. 2003. Detachment of Actinobacillus actinomycetemcomitans biofilm cells by an endogenous β-hexosaminidase activity. J Bacteriol 2003; 185: 4693-8). Dispersin B cleaves β(1,6)-linked N-acetylglucosamine polymer using a catalytic machinery similar to other family 20 hexosaminidases which cleave β(1,4)-linked N-acetylglucosamine residues. Dispersin B and similar hexosaminidases with activity in biofilms are suitable for use in the methods, physiologically acceptable anti-biofilm compositions, etc., discussed herein. The anti-poly-β-1,6-GlcNAc agents can be used with, or instead of, cellulase, discussed further below, although typically they are used together.

In one aspect the suitable, physiologically acceptable anti-biofilm compositions comprise a cellulase in an amount capable of significant biofilm degradation. Such cellulases can have activity, against for example, cellulose in a salmonella biofilm or others. Cellulase refers to a class of enzymes produced chiefly by fungi, bacteria, and protozoans that catalyze the hydrolysis of cellulose. However, there are also cellulases produced by other types of organisms such as plants and animals. Cellulases that have been used as digestive enzymes are known to be acid-stable. These include but are not limited to cellulases from *Aspergillus* species. Several different kinds of cellulases are known, which differ structurally and mechanistically. The EC number for this group of enzymes is EC 3.2.1.4. The reaction catalyzed is the endohydrolysis of 1,4-β-D-glycosidic linkages in cellulose. Other names for cellulase are: Endoglucanase, endo-1,4-β-glucanase, carboxymethyl cellulose, endo-1,4-β-D-glucanase, β-1,4-glucanase, β-1,4-endoglucan hydrolase, celludextrinase, avicelase. Cellulases have been used in vitro in the disruption of biofilms on medical implants under acidic pH conditions (Loiselle M, Anderson K W, The use of cellulase in inhibiting biofilm formation from organisms commonly found on medical implants. Biofouling 2003; 19:77-85.) In typical embodiments, the cellulase(s) herein are resistant to denaturation/inactivation at a pH range of 1.0 to 5.0 and 10 to 14, possesses hydrolytic activity across a pH span of 1 to 14, has effective hydrolytic activity within the gastric environment at a fasting pH of 1.0 to 3.0 and in the presence of food and other ingested material, and/or possesses effective hydrolytic activity at a pH of 6.5 to 7.5 encompassing physiologic ph in the small intestines and colon.

Commercial sources of cellulases, hemicellulases and other enzymes that may be used include the following: Deerland Enzymes, Kennesaw, Ga. (deerlandenzymes.com); National Enzyme Company (nationalenzyme.com), Specialty Enzymes (specialtyenzymes.com); and others. The enzymes may be derived from any suitable source such as plant, bacterial, fungal or animal sources.

In one embodiment, the physiologically acceptable anti-biofilm composition comprises cellulase, hemicellulase/pectinase complex, β-gluconase, acid protease, alkaline protease, and Serratia peptidase with at least one pharmaceutically acceptable carrier, diluents, excipients, buffers, or adjuvants. Pharmaceutically acceptable carriers or diluents, excipients, buffers, adjuvants, and the like are nontoxic to recipients at the dosages and concentrations employed.

In a further embodiment, the amount of cellulase per oral dose is about 100-300 CU, and typically about 200 CU; the amount of hemicellulase/pectinase complex is about 60-100 HSU, and typically about 80 HSU; the amount of β-gluconase is about 6-10 BGU, and typically about 8 BGU; the amount of acid protease is about 15-25 SAP, and typically about 20 SAP; and, the amount of alkaline protease is about 15-25 HUT, and typically about 20 HUT.

In still further embodiments, the amount of cellulase per oral dose ranges from 1 to 10,000 CU, the amount of hemicellulase/pectinase complex ranges from 1 to 8,000 HSU, the amount of β-gluconase ranges from 1 to 1000 BGU, the amount of acid protease ranges from 1 to 10,000 SAP, and the amount of alkaline protease ranges from 1 to 40,000 HUT.

In a further embodiment, the physiologically acceptable anti-biofilm composition comprises cellulase, hemicellulase/pectinase complex, β-gluconase, acid protease, alkaline protease, Serratia peptidase, and any one or more of the following in an amount capable an amount capable of significant biofilm degradation: disaccharides, amylase, α-amylase, β-amylase, glucoamylase, endoglucanase, xylanase, lipase, lysozyme, any enzyme such as a protease, peptidase or protease/peptidase complex with dipeptidyl peptidase IV (DPP-IV) activity, chitosanase, bromelain, papain, ficin, kiwi protease, any plant-derived protease or proteinase, or phytase.

In a further embodiment, the physiologically acceptable anti-biofilm composition is composed of cellulase, hemicellulase/pectinase complex, β-gluconase, acid protease, alkaline protease, Serratia peptidase, and any one or more of the following specific enzymes in an amount capable of biofilm degradation: 1,2-1,3-α-D-mannan mannohydrolase, 1,3-β-D-xylanxylano-hydrolase, 1,3-β-D-glucan glucanohydrolase, 1,3(1,3; 1,4)-α-D-glucan 3-glucanohydrolase, 1,3(1,3; 1,4)-β-D-glucan 3(4)-glucanohydrolase, 1,3-1,4-α-D-glucan 4-glucanohydrolase, 1,4-α-D-glucan glucanehydrolase, 1,4-α-D-glucan glucohydrolase, 1,4-(1,3:1,4)-β-D-glucan 4-glucanohydrolase, 1,4-β-D-glucan glucohydrolase, 1,4-β-D-xylan xylanohydrolase, 1,4βD-mannan mannanohydrolase, 1,5-α-L-arabinanohydrolase, 1,4-α-D-glucan maltohydrolase, 1,6-αD-glucan 6-glucanohydrolase, 2,6-β-fructan fructanohydrolase, α-dextrin 6-glucanohydrolase, α-D-galactoside galactohydrolase, α-D-glucoside glucohydrolase, α-D-mannoside manno-hydrolase, acylneuraminyl hydrolase, Aerobacter-capsular-polysaccharide galactohydrolase, βD-fructofuranoside fructohydrolase, β-D-fucoside fucohydrolase, α-D-fructan fructohydrolase, β-D-galactoside galactohydrolase, β-D-glucoside glucohydrolase, β-D-glucuronoside, glucuronosohydrolase, β-D-mannoside mannohydrolase, β-N-acetyl-D-hexosaminide N-acetylhexosamino hydrolase, cellulose-sulfate sulfohydrolase, collagenase, dextrin 6-α-D-glucano-hydrolase, glycoprotein-phosphatidylinositol phosphatidohydrolase, hyaluronate 4-glycano-hydrolase, hyaluronoglucuronidase, pectin pectylhydrolase, peptidoglycan N-acetyl-muramoylhydrolase, phosphatidylcholine 2-acylhydrolase, phosphatidylcholine 1-acylhydrolase, poly(1,4-α-D-galacturonide), poly (1,4-(N-acetyl-β-D-glucosaminide))-glycanohydrolase, proteases, sucrose α-glucosidase, triacylglycerol acylhydrolase, triacylglycerol protein-acylhydrolase.

Another group of enzymes that may be employed in the methods, etc. herein is a sub-group of serine proteases commonly designated as subtilisins. A subtilisin is a serine protease produced by Gram-positive bacteria or fungi. The amino acid sequences of a number of subtilisins have been determined, including at least six subtilisins from Bacillus strains, namely, subtilisin 168, subtilisin BPN, subtilisin Carlsberg, subtilisin DY, subtilisin amylosachariticus, and *mesentericopeptidase,* one subtilisin from an actinomycetales, thermitase from *Thermoactinomyces vulgaris,* and one fungal subtilisin, proteinase K from Tritirachium album.

An exemplary lipase as discussed above can be a microbial lipase. As such, the lipase may be selected from yeast lipases, e.g., *Candida,* and bacterial lipases, e.g. *Pseudomonas* or *Bacillus,* lipases; or fungal, e.g., *Humicola* or *Rhizomucor.*

Examples of amylases useful in the methods, etc., herein include Bacillus amylases, e.g., Bacillus stearothermophilus amylase, Bacillus amyloliquefaciens amylase, Bacillus subtilis amylase or Bacillus licheniformis amylase or Aspergillus amylases, e.g. Aspergillus niger or Aspergillus oryzae amylase.

Another group of enzymes useful in the methods, etc., herein include pectinases belonging to the enzyme classes polygalacturonases (EC3.2.1.15), pectinesterases (EC3.2.1.11), pectin lyases (EC4.2.2.10) and hemicellulases such as endo-1,3-β-xylosidase (EC 3.2.1.32), xylan 1,4-β-xylosidase (EC 3.2.1.37) and α-L-arabinofuranosidase (EC 3.2.1.55). A suitable source organism for pectinases may be Aspergillus niger or Aspergillus aculeatus.

Lysozyme, also known as muramidase or N-*acetylmuramide glycanhydrolase*, is a 14.4 kilodalton enzyme (EC 3.2.1.17) that damages bacterial cell walls by catalyzing hydrolysis of 1,4-β-linkages between N-acetylmuramic acid and N-acetyl-D-glucosamine residues in a peptidoglycan and between N-acetyl-D-glucosamine residues in chitodextrins. Lysozyme is found in saliva, tears, and polymorphonucleocytes and has known antibacterial activity. The enzyme functions by attacking peptidoglycans (found in the cells walls of bacteria, especially Gram-positive bacteria) and hydrolyzing the glycosidic bond that connects N-acetylmuramic acid with the fourth carbon atom of N-acetylglucosamine. Lysozyme has been used in the treatment of otitis media and sinusitis (U.S. Pat. No. 7,060,674). Oral lysozyme compositions have been used in the treatment of various conditions in humans, including arthritis (U.S. Pat. No. 7,229,809).

Another enzyme that may be employed in the methods, etc. herein is deoxyribonuclease I (DNase I), a phosphodiesterase capable of hydrolyzing polydeoxyribonucleic acid. DNase I has been purified from various species to various degrees. DNase I, when inhaled, affects the capability of *P. aeruginosa* to form biofilms in the lungs in the initial development stages. DNase I hydrolyzes the DNA present in sputum/mucus of cystic fibrosis patients and reduces viscosity in the lungs, promoting improved clearance of secretions. Enzymes that are acid-stable are candidates for use in conjunction with the methods, physiologically acceptable anti-biofilm compositions, etc., discussed herein. DNase I activities are classifiable into three groups on the basis of their different tissue distributions of DNase I. DNase I of parotid type is secreted from the parotid gland and must pass through the very acidic conditions in the stomach.

The physiologically acceptable anti-biofilm compositions, methods, etc., herein are to be taken by mouth, typically at least 1 hour before or 1 hour after a meal or consumption of food. The physiologically acceptable anti-biofilm compositions, methods, etc., herein are typically to be taken 2 to 4 times per day (other intervals may be appropriate in certain circumstances) and the regimen is typically to be followed for an extended period, for example at least about 1 or 2 months.

The enzyme preparation may be combined with a natural antimicrobial such as oil of oregano, berberine, or undecylenic acid or with a prescription antibiotic or antimicrobial. The enzyme preparation may be combined with the oral intake of one or more probiotic microorganisms. The World Health Organization defines probiotic organisms as live microorganisms that when administered in adequate amounts confer a health benefit on the host. The enzyme preparation may be combined with one or more prebiotics. A prebiotic is defined as "selectively fermented ingredients that allow specific changes, both in the composition and/or activity in the gastrointestinal microflora that confer benefits upon host well-being and health." (Roberfroid M. Prebiotics: the concept revisited. J Nutr 2007; 137(3 Suppl 2):830S-7S.)

Methods related to the compositions, etc., herein include methods of screening, making and using, including for the manufacture of medicaments.

For example, the methods include methods of screening for a physiologically acceptable anti-biofilm composition suitable for oral administration to a mammal while retaining effectiveness in the gut, the method comprising, providing a significant plurality of samples of a live target biofilm on at least one substrate; applying to each of the plurality of samples one of range of doses of a candidate anti-biofilm agent selected from the group comprising acid-stable cellulase and an anti-biofilm anti-polymeric β-1,6-N-acetyl-D-glucosamine (poly-β-1,6-GlcNAc) agent, under conditions The samples of the target biofilm can grow absent a significant anti-biofilm effect due to the candidate anti-biofilm agent; and, determining whether each of the range of doses of candidate anti-biofilm agent inhibited growth of its respective sample.

The methods can further comprise screening both the anti-biofilm acid-stable cellulase and the anti-biofilm anti-poly-β-1,6-GlcNAc agent. The anti-biofilm anti-poly-β-1,6-GlcNAc agent can be a hexosaminidase such as *Dispersin B*. The methods can further comprise screening at least one of an acid-stable hemicellulase/pectinase complex, β-gluconase, acid protease, *alkaline protease*, or *Serratia peptidase*. The amount of cellulase can be equivalent to a dose of about 100-300 CU, the amount of hemicellulase/pectinase complex can be about 60-100 HSU, the amount of β-gluconase can be about 6-10 BGU, the amount of acid protease can be about 15-25 SAP, and the amount of alkaline protease can be about 15-25 HUT.

The methods can also comprise screening at least one an acid-stable agent selected from the following: a disaccharide; amylase; α-amylase; β-amylase; glucoamylase; endoglucanase; xylanase; lipase; lysozyme; an enzyme with dipeptidyl peptidase IV (DPP-IV) activity; chitosanase; bromelain; papain; ficin; kiwi protease; any plant-derived protease or proteinase, or phytase. The lipase can be a microbial lipase, such as from at least one of *Candida, Pseudomonas, Bacillus, Humicola* or *Rhizomucor*. The amylase can be at least one of a *Bacillus* amylase or *Aspergillus* amylase. The screen can comprise at least one pectinase that can be at least one of a polygalacturonase (EC3.2.1.15), pectinesterase (EC3.2.1.11), pectin lyase (EC4.2.2.10) or hemicellulase. The pectinase can be at least one an *Aspergillus niger* pectinase or *Aspergillus aculeatus* pectinase.

The methods can further comprise screening at least one of the following: 1,2-1,3-α-D-mannan mannohydrolase, 1,3-β-D-xylanxylanohydrolase, 1,3-β-D-glucan glucanohydrolase, 1,3 (1,3; 1,4)-α-D-glucan 3-glucanohydrolase, 1,3 (1,3; 1,4)-β-D-glucan 3(4)-glucanohydrolase, 1,3-1,4-α-D-glucan 4-glucanohydrolase, 1,4-α-D-glucan glucanehydrolase, 1,4-α-D-glucan glucohydrolase, 1,4-(1,3: 1,4)-β-D-glucan 4-glucanohydrolase, 1,4-β-D-glucan glucohydrolase, 1,4-β-D-xylan xylanohydrolase, 1,4-β-D-mannan mannanohydrolase, 1,5-α-L-arabinano-hydrolase, 1,4-α-D-glucan maltohydrolase, 1,6-α-D-glucan 6-glucanohydrolase, 2,6-β-fructan fructanohydrolase, α-dextrin 6-glucanohydrolase, α-D-galactoside galactohydrolase, α-D-glucoside glucohydrolase, α-D-mannoside mannohydrolase, acylneuraminyl hydrolase, Aerobacter-capsular-polysaccharide galactohydrolase, β-D-fructofuranoside fructohydrolase, β-D-fucoside fucohydrolase, α-D-fructan fructohydrolase, β-D-galactoside galactohydrolase, β-D-glucoside glucohydrolase, β-D-glucuronoside, glucuronosohydrolase, β-D-mannoside manno-hydrolase, β-N-acetyl-D-hexosaminide N-acetylhexosamino hydrolase, cellulose-sulfate sulfo-hydrolase, collagenase, dextrin 6-α-D-glucanohydrolase, glycoprotein-phosphatidylinositol phosphatidohydrolase, hyaluronate 4-glycanohydrolase, hyaluronoglucuronidase, pectin pectyl-hydrolase, peptidoglycan N-acetylmuramoylhydrolase, phosphatidylcholine 2-acylhydrolase, phosphatidylcholine 1-acylhydrolase, poly (1,4-α-D-galacturonide), poly(1,4-(N-acetyl-β-D-glucosaminide))-glycanohydrolase, proteases, sucrose α-glucosidase, triacylglycerol acyl-hydrolase, triacylglycerol protein-acylhydrolase.

The methods can further comprise screening an acid-stable subtilisin, an acid-stable DNAse I, oil of oregano, berberine, undecylenic acid, a prescription antibiotic, a prescription antimicrobial, a probiotic microorganism or a prebiotic.

In some aspects, the methods comprise inhibiting a gastrointestinal biofilm infection in a mammal, the method comprising: identifying the presence of the gastrointestinal biofilm infection, orally administering to the mammal a therapeutically effective amount of at least one anti-biofilm agent comprising an acid-stable cellulase or an anti-polymeric β-1,6-N-acetyl-D-glucosamine (poly-β-1,6-GlcNAc) agent in at least one pharmaceutically acceptable carrier, in an amount and for a time sufficient to cause significant biofilm degradation within the gastrointestinal system of the mammal. In further embodiments the methods comprise administering one or more of the other aspects of the compositions, etc., herein.

The composition can be for use as an active therapeutic substance, for use in the manufacture of a medicament for inhibiting or treating a gastrointestinal biofilm in a mammal, or for manufacturing a medicament able to reduce symptoms associated with a gastrointestinal biofilm in a human patient, for example comprising combining a pharmaceutically effective amount of at least one of an anti-biofilm acid-stable cellulase or an anti-biofilm anti-polymeric β-1,6-N-acetyl-D-glucosamine (poly-β-1,6-GlcNAc) agent in an amount capable of significant biofilm degradation with at least one of a pharmaceutically acceptable carrier, adjuvant, excipient, buffer and diluent.

Exemplary Biofilm Targets

Exemplary target biofilm organisms, including both indigenous and biofilm infectious organisms are discussed below.

*Enterococci*

*Enterococci*, although part of the normal flora of the human gastrointestinal tract, have been recognized as an important cause of nosocomial infection for over two decades and are commonly implicated in urinary tract infections, bacteremia, intra-abdominal and surgical wound infections, catheter-related infections, and endocarditis.

*Staphylococcus*

Pathogenic staphylococci can form biofilms in which they show a higher resistance to antibiotics and the immune defense system than their planktonic counterparts. *Staphylococcus aureus* is a common pathogen associated with nosocomial infections. It can persist in clinical settings and gain increased resistance to antimicrobial agents through biofilm formation. Staphylococcus aureus is among the leading pathogens causing bloodstream infections able to form biofilms on host tissue and indwelling medical devices and to persist and cause disease. Infections caused by S. aureus are becoming more difficult to treat because of increasing resistance to antibiotics (e.g., vancomycin or methicillin-resistant *Staphylococcus aureus*). In a biofilm environment particularly, microbes exhibit enhanced resistance to antimicrobial agents.

*Pseudomonas*

The human opportunistic pathogen, *Pseudomonas aeruginosa*, is a major cause of infectious-related mortality among the critically ill patients, and carries one of the highest case fatality rates of all gram-negative infections. Although the lungs have been traditionally considered to be a major site of *P. aeruginosa* infection among critically ill patients, a significant number of these infections arise as a result of direct contamination of the airways by the gastrointestinal flora or by hematogenous dissemination from the intestine to the lung parenchyma. *Pseudomonas aeruginosa* causes severe infections in immunologically compromised patients and is a major pathogen in cystic fibrosis patients. An important virulence mechanism is the formation of a mucoid biofilm. Secreted alginate is a crucial constituent of the mucoid biofilm matrix. However, alginate-negative mutants of *P. aeruginosa* are also able to form nonmucoid biofilms, showing an architecture different from that of biofilms formed by alginate-overproducing mucoid *P. aeruginosa* (Nivens D E, Ohman D E, Williams J, Franklin M J. Role of alginate and its 0 acetylation in formation of Pseudomonas aeruginosa microcolonies and biofilms. J Bacteriol 2001; 183:1047-57; Wozniak D J, Wyckoff T J, Starkey M, Keyser R, Azadi P, O'Toole G A, Parsek M R. Alginate is not a significant component of the extracellular polysaccharide matrix of PA14 and PAO1 *Pseudomonas aeruginosa* biofilms. Proc Natl Acad Sci USA 2003; 100:7907-12.)

*Helicobacter pylori*

*H. pylori* is one of the more common human pathogens infecting 50% of the world's population. It is associated with duodenal ulcers, gastric ulcers, gastritis, and gastric carcinoma. Treatment of *H. pylori* is difficult involving multidrug regimens and lengthy treatment periods. There is a 10-20% relapse rate. Recent studies document the importance of biofilms in the pathogenesis of *H. pylori* disease. (Coticchia J M et al. Presence and density of *Helicobacter pylori* biofilms in human gastric mucosa in patients with peptic ulcer disease. J Gastrointest Surg. 2006; 10:883-9) An oral multienzyme formulation holds great promise to facilitate the elimination of *H. pylori* biofilm and the eradication of *H. pylori* pathogens thereby reducing the risk of gastritis, peptic ulcer disease, and gastric cancer.

*Listeria*

The foodborne pathogen *Listeria* is the causative agent of listeriosis, a severe disease where the overt form has a severe mortality greater than 25%. Listeria monocytogenes can survive and grow over a wide range of environmental conditions such as refrigeration temperatures, low pH and high salt concentration. This allows the pathogen to overcome food preservation and safety barriers, and pose a potential risk to human health. Listeria monocytogenes may specifically be found in raw foods, such as unpasteurized fluid milk, raw vegetables, raw and cooked poultry. It has the ability to grow at low temperatures; thus, allowing it to grow in refrigerated foods. Listeria monocytogenes was thought to be exclusively associated as infections in animals, but recently, this pathogenic species has also been isolated, in its dormant form, in the intestinal tract of small percentage of the human population (Rouquette C, Berche P. The pathogenesis of infection by Listeria monocytogenes. Microbiologia 1996; 12:245-58).

*Campylobacter*

*Campylobacter jejuni* is a species of curved, rod-shaped, Gram-negative microaerophilic, bacteria commonly found in animal feces. It is one of the most common causes of human gastroenteritis in the world. Food poisoning caused by *Campylobacter* species can be severely debilitating but is rarely life-threatening. It has been linked with subsequent development of Guillain-Barre syndrome (GBS), which usually develops two to three weeks after the initial illness. Contaminated food is a major source of isolated infections, with incorrectly prepared meat and poultry normally the source of the bacteria. Infection with *C. jejuni* usually results in enteritis, which is characterized by abdominal pain, diarrhea, fever, and malaise. The major gastrointestinal pathogen *Campylobacter jejuni* is shown to exist as three forms of monospecies biofilm in liquid culture. (Joshua G W, Guthrie-Irons C, Karlyshev A V, Wren B W. Biofilm formation in *Campylobacter jejuni*. Microbiology 2006; 152(Pt 2):387-96.)

*Bacillus anthracis*

*Bacillus anthracis* is a Gram-positive, endospore-forming bacterium and is the aetiological agent of pulmonary, gastrointestinal and cutaneous anthrax. In endemic areas in which humans and livestock interact, chronic cases of cutaneous anthrax are commonly reported. Currently, there are few data known to the inventor that account for the importance of the biofilm mode of life in *B. anthracis*, yet biofilms have been characterized in other pathogenic and non-pathogenic *Bacillus* species, including *Bacillus cereus* and *Bacillus subtilis*, respectively. *B. anthracis* readily forms biofilms which are inherently resistant to commonly prescribed antibiotics. (Lee K, Costerton J W, Ravel J, Auerbach R K, Wagner D M, Keim P, Leid J G. Phenotypic and functional characterization of *Bacillus anthracis* biofilms. Microbiology 2007; 153(Pt 6):1693-701.)

*Yersinia*

Yersiniosis is an infectious disease caused by a bacterium of the genus *Yersinia*. In the United States, most human illness is caused by one species, *Y. enterocolitica*. Infection with *Y. enterocolitica* occurs most often in young children. Common symptoms in children are fever, abdominal pain, and diarrhea. Gastrointestinal symptoms are common in both the acute and chronic states of yersiniosis. Infection is most often acquired by eating contaminated food, especially raw or undercooked pork products. Drinking contaminated unpasteurized milk or untreated water can also transmit the infection.

*Yersinia pestis*, the causative agent of bubonic plague, is transmitted to rodents and humans by the bites of fleas whose proventriculi are blocked by a dense mass of the biofilm bacteria. (Tan L, Darby C. A movable surface: formation of *Yersinia* sp. biofilms on motile *Caenorhabditis elegans*. J. Bacteriol. 2004; 186:5087-92.) The blockage starves the flea and stimulates it to bite repeatedly in search of blood meals, thus spreading the bacteria to new hosts. Biofilm models using Caenorhabditis elegans may be used to identify enzymes that kill Yersinia biofilms (Styer K L, Hopkins G W, Bartra S S, Plano G V, Frothingham R, Aballay A. Yersinia pestis kills Caenorhabditis elegans by a biofilm-independent process that involves novel virulence factors. EMBO reports 2005; 10:992-7.)

Brucella Species

Humans are generally infected in one of three ways: eating or drinking something that is contaminated with Brucella, breathing in the organism (inhalation), or having the bacteria enter the body through skin wounds. The most common way to be infected is by eating or drinking contaminated milk products.

Salmonella

*Salmonella enterica*, a foodborne pathogen that causes salmonellosis, is caused by the ingestion of bacteria that invade the intestinal epithelium and multiply there. *Salmonella enterica* is known to form biofilms, and its attachment to, and growth on, eukaryotic cells is facilitated by exopolysaccharides (Ledeboer & Jones, 2005). Most persons infected with *Salmonella* develop diarrhea, fever, and abdominal cramps 12 to 72 hours after infection. The illness usually lasts 4 to 7 days, and most persons recover without treatment. However, in some persons the diarrhea may be so severe that the patient needs to be hospitalized. In these patients, the *Salmonella* infection may spread from the intestines to the blood stream, and then to other body sites and can cause death unless the person is treated promptly.

Shigella

There are several different kinds of *Shigella* bacteria: *Shigella sonnei*, also known as "Group D" *Shigella*, accounts for over two-thirds of the shigellosis in the United States. Shigellosis is an infectious disease caused by a group of bacteria called *Shigella*. Most who are infected with *Shigella* develop diarrhea, fever, and stomach cramps starting a day or two after they are exposed to the bacterium. Some *Shigella* bacteria have become resistant to antibiotics. A second type, *Shigella flexneri*, or "group B" *Shigella*, accounts for almost all of the rest. Other types of *Shigella* continue to be important causes of disease in the developing world. One type found in the developing world, *Shigella dysenteriae* type 1, causes deadly epidemics there.

Typhi (Typhoid Fever)

*Salmonella enterica* serovar *Typhi* causes typhoid fever, an enteric fever that is potentially fatal. Asymptomatic carriers may carry bacteria in the gallbladder. *Salmonella typhi* lives only in humans. Persons with typhoid fever carry the bacteria in their bloodstream and intestinal tract. In addition, a small number of persons, called carriers, recover from typhoid fever but continue to carry the bacteria. Both ill persons and carriers shed *S. typhi* in their feces (stool). *Salmonella typhi* is transmitted in contaminated food, water and beverages. A system was recently developed to analyze salmonella biofilm formation on glass coverslips (Prouty A M, Schwesinger W H, Gunn J S. Biofilm formation and interaction with the surfaces of gallstones by *Salmonella* spp. Infect Immun 2002; 70:2640-9.)

*Escherichia coli*

Enterotoxigenic *Escherichia coli* targets the small intestine where the barrier effect of the autochthonous microflora is low due to higher acidity and peristaltic movements in this region. This organism adheres to and colonizes the mucus in order to elicit a pathogenic effect (Knutton S, Lloyd D R, Candy D C, McNeish A S. In vitro adhesion of enterotoxigenic *Escherichia coli* to human intestinal epithelial cells from mucosal biopsies. Infect Immun 1984; 44:514-8.) This means that the pathogen and/or its toxins can readily adhere to exposed eneterocytes and invade the host.

*Vibrio cholerae* (Cholera)

*Vibrio cholerae* is a Gram-negative, facultative pathogen that is the causative agent of cholera, a devastating diarrheal disease that affects millions of people in the developing world each year; it survives in aqueous reservoirs, probably in the form of biofilms.

*Entamoeba histolytica*

Invasive intestinal amebiasis, caused by *Entamoeba histolytica*, is initiated with attachment of trophozoites to the colonic mucous layer, mucous disruption and/or depletion, and adherence to and cytolysis of host epithelial and inflammatory cells. A current working model of intestinal amebiasis suggests that the microenvironment of the host intestine, particularly intestinal mucins and the bacterial biofilm, may influence the behavior of pathogenic amebae. Enzymes that disrupt bacterial biofilm will be useful in the inhibition and treatment of amebiasis.

EXAMPLES

Example 1

Documenting a Multienzyme Formulation Antibiofilm Activity

Initial experiments were conducted with an multienzyme formulation consisting of Cellulase—2000 CU, Glucoamylase—50 AGU, Hemicellulase/Pectinase—300 HSU, Beta-glucanase—100 BGU, Protease/peptidase complex w/DPP-IV activity—100,000 HUT, Chitosanase—100 units, Lysozyme—200,000 SHU, and Serratia peptidase—1000 units. These enzyme activities were contained in a 500 mg mixture which included 20 mg of L-leucine. The multizyme formulation was tested over a series of dilutions from 50 mg/mL to 0.34 mg/mL. Dilutions were made in sterile Cation Adjusted Mueller Hinton Broth (CAMHB) or Sabouraud Dextrose Broth (SDB) for Yeasts.

The multienzyme formulation was tested in vitro against *Escherichia coli* O157:H7, *Kelbsiella pneumoniae* ATCC 4352, *Candida paratropicalis* ATCC 99916, and *Candida albicans* SJ2083133. Although *Candida albicans* forms significant biofilms in vivo, it is not a predictable former of biofilms in vitro, but it was incorporated in the experiment because of its clinical importance.

The experimental process for high-throughput antimicrobial susceptibility testing used a Calgary Biofilm Device assay (MBEC.TM.P&G, Innovatech). This standard protocol may be divided into a series of steps, which are detailed below.

Growing the Organisms and Forming the Biofilms a. Using a cryogenic stock (at −70° C.), streak out a first sub-culture of the bacterial organisms listed above on trypticase soy agar (TSA).

b. Incubate at 37° C. for 24 hours and store the plate wrapped in parafilm at 4° C.

c. From the first sub-culture, streak out a second sub-culture on TSA. Incubate at 37° C. for 24 hours. The second sub-culture should be used within 24 hours starting from the time it was first removed from incubation.

d. Using the second sub-culture create an inoculum in 3 mL sterile water that matches a 0.5 McFarland Standard (1.5.times.10.sup.8 cells per mL) in a glass test tube using a sterile cotton swab.

e. Dilute this solution 1:30 in CAMHB (or 1:10 in SDB for yeast).

f. Invert the diluted organism 3-5 times to achieve uniform mixing of the organism.

g. The cell density will be confirmed by serially diluting and spot plating triplicate samples of the inoculum on TSA or SA.

h. The remaining diluted organism (22 mL) will be placed in the troughs of a 96 peg MBEC HTP device.

i. Place the lid of the 96 peg MBEC device on the bottom plate containing organism.

j. Place the device on a rocker in a humidified incubator at 37° C. for 24 hours set at 3-4 rocks per minute.

k. Poly-L-lysine plates were used to culture *C. paratropicalis* and *C. albicans*. These were prepared by Diluting 0.1% (w/v) poly L-lysine solution (Sigma P8920) 10X in deionized water which was filtered sterilized.

Sterile 96-well microtiter plates were prepared under a laminar flow hood. Each plate included sterility controls, growth controls, and antibiotic challenge well. Gentamycin was used for the bacteria and amphotericin B for the Candida in concentration ranges from 1024 mcg/mL to 1 mcg/mL. Organisms were tested using exposure time points of 24 hours. One plate was assessed per organism per time point. Triplicate samples were used to assess the impact of the multienzyme formulation on biofilm formation.

Planktonic minimal inhibitory concentration (MIC) and minimal bacteriocidal concentration MBC were determined after incubating the challenge plate at 35 ±2° C. for 24 hours. MIC determination was done by visual inspection. The MIC is defined as the minimum concentration that inhibits growth of the organism. MBC results are determined following the 24 hour incubation by +/− growth.

Minimum biofilm eradication concentration (MBEC) results were determined following the 24 hour incubation from the MBEC panels using the plate reader in conjunction with Log 10 reduction data. Turbidity was assessed visually in the wells of the recovery plate. Alternatively, a microtiter plate reader was used to obtain optical density measurements at 630 nm ($OD_{630}$). Clear wells ($OD_{630}<0.1$) are evidence of biofilm eradication. The MBEC is defined as the minimum concentration of antibiotic that inhibits growth of the biofilm.

The results of experiment 1 were as follows:

a. *Escherichia coli* O157:117—No MIC, MBC and MBEC cut-off points were observed with the multienzyme tested. The multienzyme formulation had antibiofilm activity at all but the 2 lowest tested concentrations. The data are tabulated below:

| Log Reduction Dilution (mg/mL) | Filtered | Plate-Enzyme Log Reduction (GC-Test) | | | | | Statistics* Log Reduction vs. GC | |
|---|---|---|---|---|---|---|---|---|
| | | 1 | 2 | 3 | Mean | ±SD | P | S/NS* |
| 50 | −0.42 | 0.7 | 0.31 | 0.16 | 0.39 | 0.28 | 0.00 | S |
| 25 | 0.53 | 1.18 | 1.37 | 1.53 | 1.36 | 0.17 | 0.00 | S |
| 12.5 | 1.7 | 1.64 | 2 | 1.64 | 1.76 | 0.21 | 0.00 | S |
| 6.25 | 2.78 | 1.7 | 2 | 1.58 | 1.76 | 0.22 | 0.00 | S |
| 3.13 | 0.78 | 0.2 | 0.53 | 0.78 | 0.5 | 0.29 | 0.00 | S |
| 1.56 | 0.58 | 0.78 | 1 | 0.88 | 0.89 | 0.11 | 0.00 | S |
| 0.78 | 0.14 | 0.25 | 0.23 | 0.23 | 0.23 | 0.01 | 0.00 | S |

*Non-pairwise, two-tailed Student's T-test (for statistical significance, $p \leq 0.05$)

b. *Klebsiella pneumoniae* ATCC 4352—For MIC and MBC there were no observed cut-off points at the tested concentrations. The MBEC value for the multienzyme formulation was 6.25 mg/mL. The multienzyme formulation had antibiofilm activity with log reductions of 3.0-3.8 at the 50-6.25 mg/mL concentrations and .about.1.5 for the lower concentrations. The data are tabulated below:

| Log Reduction Dilution (mg/mL) | Filtered | Plate-Enzyme Log Reduction (GC-Test) | | | | | Statistics* Log Reduction vs. GC | |
|---|---|---|---|---|---|---|---|---|
| | | 1 | 2 | 3 | Mean | ±SD | P | S/NS* |
| 50 | 3.65 | 3.87 | 3.39 | 4.35 | 3.87 | 0.48 | 0.00 | S |
| 25 | 3.02 | 3.35 | 3.65 | 3.57 | 3.52 | 0.16 | 0.00 | S |
| 12.5 | 2.87 | 3.17 | 3.04 | 3.04 | 3.09 | 0.07 | 0.00 | S |
| 6.25 | 2.04 | 3.65 | 3.44 | 3.35 | 3.48 | 0.15 | 0.00 | S |
| 3.13 | 1.57 | 1.23 | 2.35 | 1.5 | 1.69 | 0.58 | 0.00 | S |
| 1.56 | 0.44 | 1.39 | 1.5 | 1.5 | 1.46 | 0.06 | 0.00 | S |
| 0.78 | 0.44 | 1.5 | 1.74 | 1.74 | 1.66 | 0.14 | 0.00 | S |
| 0.39 | 1.65 | 1.14 | 2.04 | 1.57 | 1.58 | 0.45 | 0.00 | S |

*Non-pairwise, two-tailed Student's T-test (for statistical significance, $p \leq 0.05$)

c. *Candida paratropicalis* ATCC 99916—No MIC, MBC and MBEC cut-off values were observed at the tested concentrations. The multienzyme formulation had antibiofilm activity with a log reduction at the concentrations between 25 mg/mL and 1.56 mg/mL. The data are tabulated below:

| Log Reduction Dilution (mg/mL) | Filtered | Plate-Enzyme Log Reduction (GC-Test) | | | | | Statistics* Log Reduction vs. GC | |
|---|---|---|---|---|---|---|---|---|
| | | 1 | 2 | 3 | Mean | ±SD | P | S/NS* |
| 50 | −0.40 | −0.36 | −0.51 | −0.36 | −0.41 | 0.08 | 0.00 | S |
| 25 | −0.54 | −0.06 | 0.16 | −0.27 | −0.06 | 0.21 | 0.00 | S |
| 12.5 | 0.94 | 1.34 | 1.16 | 1.64 | 1.38 | 0.24 | 0.00 | S |
| 6.25 | 1.16 | 0.94 | 1.64 | 1.34 | 1.3 | 0.35 | 0.00 | S |

-continued

| Log Reduction | | Plate-Enzyme Log Reduction (GC-Test) | | | | | Statistics* Log Reduction vs. GC | |
|---|---|---|---|---|---|---|---|---|
| Dilution (mg/mL) | Filtered | 1 | 2 | 3 | Mean | ±SD | P | S/NS* |
| 3.13 | 1.34 | 1.16 | 1.04 | 1.64 | 1.28 | 0.32 | 0.00 | S |
| 1.56 | 0.46 | 1.34 | 1.16 | 1.16 | 1.22 | 0.1 | 0.00 | S |
| 0.78 | 0.94 | 1.04 | 0.6 | −0.06 | 0.52 | 0.55 | 0.00 | S |
| 0.39 | 0.04 | 0.34 | 1.04 | −0.06 | 0.44 | 0.56 | 0.00 | S |

*Non-pairwise, two-tailed Student's T-test (for statistical significance, p ≤ 0.05)

d. *Candida albicans* SJ2083133 did not reliably make biofilm and the multienzyme could not be assessed.

Example 2

Experiment 2 assessed the above multienzyme formulation without and with 125 mg of Disodium ethylene diamine tetraacetic acid for antibiofilm activity against *Staphylococcus aureus* ATCC 29213 and *Staphylococcus aureus* MRSA U of C #18. Growth medium and conditions were TSB/TSA, aerobic, and 35 ±2° C. The experimental design and conditions were as described above for experiment 1.

The results of experiment 2 were as follows:

*Staphylococcus aureus* ATCC 29213—The MIC, MBC and MBEC for the multienzyme formulation were found to have no cut-off points at the tested concentrations. The multienzyme formulation had antibiofilm activity at all but the lowest tested concentrations. The log reductions versus growth controls (GC) were significant at the P<0.05 level. The data are tabulated below:

| Log Reduction | | Plate-Enzyme Log Reduction (GC-Test) | | | | |
|---|---|---|---|---|---|---|
| Dilution (mg/mL) | Filtered | 1 | 2 | 3 | Mean | ±SD |
| 50 | 2.38 | 1.9 | 1.9 | 1.58 | 1.79 | 0.19 |
| 25 | 3.15 | 3.01 | 2.81 | 2.38 | 2.73 | 0.32 |
| 12.5 | 3.55 | 1.65 | 1.81 | 0.53 | 1.33 | 0.7 |
| 6.25 | 1.38 | 1.78 | 2.74 | 2.08 | 2.2 | 0.49 |
| 3.13 | 0.85 | 3.01 | 1.55 | 1.74 | 2.1 | 0.79 |
| 1.56 | 1.85 | 2.16 | 2.01 | 1.81 | 1.99 | 0.17 |
| 0.78 | 0.44 | −0.19 | 2.65 | 0.78 | 1.08 | 1.44 |
| 0.34 | 0.08 | 0.38 | −0.10 | 0.53 | 0.27 | 0.33 |

*Staphylococcus aureus* ATCC 29213—The MBEC for the multienzyme formulation with EDTA was found to have no cut-off point at the tested concentrations. The MBC for multienzyme/EDTA was observed to have the cut-off point at 3.13 mg/mL and the MIC for multienzyme/EDTA was observed to have the cut-off point at 1.56 mg/mL. The log reduction for multienzyme/EDTA much greater than the log reduction for the multienzyme formulation and at a much lower concentration for multienzyme/EDTA showing that multienzyme/EDTA has a much greater effect the eradication of the bacterial biofilm. The data are tabulated below.

| Log Reduction | | Plate-Enzyme Log Reduction (GC-Test) | | | | |
|---|---|---|---|---|---|---|
| Dilution (mg/mL) | Filtered | 1 | 2 | 3 | Mean | ±SD |
| 50 | 2.85 | 2.38 | 3.85 | 1.85 | 2.69 | 1.03 |
| 25 | 3.55 | 2.81 | 5.85 | 5.85 | 4.84 | 1.76 |
| 12.5 | 2.38 | 3.55 | 5.85 | 5.85 | 5.09 | 1.33 |
| 6.25 | 2.71 | 3.38 | 3.85 | 5.85 | 4.36 | 1.32 |
| 3.13 | 3.85 | 5.85 | 5.85 | 5.85 | 5.85 | 0 |
| 1.56 | 2.65 | 3.85 | 3.38 | 3.55 | 3.59 | 0.24 |
| 0.78 | 2.16 | 5.85 | 5.85 | 3.85 | 5.19 | 1.16 |
| 0.34 | 0.95 | 0.3 | 0.65 | 0.49 | 0.48 | 0.18 |

*Staphylococcus aureus* MRSA 399—The MIC, MBC and MBEC for the multienzyme formulation were found to have no cut-off point at the tested concentrations. The multienzyme formulation exhibited antibiofilm activity across a range of concentrations although the activity was inconsistent. Variability among the triplicate samples is noted. The data are tabulated below.

| Log Reduction | | Plate-Enzyme Log Reduction (GC-Test) | | | | |
|---|---|---|---|---|---|---|
| Dilution (mg/mL) | Filtered | 1 | 2 | 3 | Mean | ±SD |
| 50 | −1.27 | 3.73 | 0.73 | 3.73 | 2.73 | 1.73 |
| 25 | 3.73 | 3.73 | 0.25 | 3.73 | 2.57 | 2.01 |
| 12.5 | −0.75 | −2.75 | 3.73 | −0.88 | 0.03 | 3.33 |
| 6.25 | 1.72 | 3.73 | 3.73 | −0.05 | 2.47 | 2.18 |
| 3.13 | 1.42 | 1.72 | 0.42 | 3.73 | 1.96 | 1.66 |
| 1.56 | −0.48 | −0.32 | −1.88 | −0.12 | −0.77 | 0.96 |
| 0.78 | −1.88 | −0.27 | −1.45 | 0.65 | −0.36 | 1.05 |
| 0.34 | −1.39 | 1.72 | −0.27 | 3.73 | 1.72 | 2 |

Example 3

*Staphylococcus aureus* MRSA 399—The MBEC for the multienzyme formulation with EDTA was found to have no cut-off point at the tested concentrations. The MIC and MBC for the multienzyme formulation with EDTA were observed to have the cut-off point at 1.56 mg/mL. The multienzyme formulation with EDTA more potent and more effective in the eradication of the bacterial biofilm compared to the multienzyme since the multienzyme formulation with EDTA's largest log reduction is at a lower concentration than the multienzyme's largest log reduction. The observation that the enzyme/EDTA for MIC and MBC activities indicates significant antimicrobial as well as antibiofilm properties. The data are tabulated below.

| Log Reduction | | | | | | |
|---|---|---|---|---|---|---|
| Dilution | | Plate-Enzyme Log Reduction (GC-Test | | | | |
| (mg/mL) | Filtered | 1 | 2 | 3 | Mean | ±SD |
| 50 | −1.60 | 0.61 | 3.73 | −0.27 | 1.35 | 2.1 |
| 25 | −2.97 | 3.73 | 3.73 | −1.75 | 1.9 | 3.16 |
| 12.5 | 0.95 | 3.73 | 3.73 | 3.73 | 3.73 | 0 |
| 6.25 | 3.73 | 0.73 | 3.73 | 0.42 | 1.63 | 1.83 |
| 3.13 | 3.73 | 3.73 | 3.73 | 1.72 | 3.06 | 1.16 |
| 1.56 | 1.72 | 1.72 | 3.73 | 3.73 | 3.06 | 1.16 |
| 0.78 | 0.73 | 3.73 | 3.73 | 3.73 | 3.73 | 0 |
| 0.34 | 3.73 | 3.73 | 3.73 | 3.73 | 3.73 | 0 |

All terms used herein, are used in accordance with their ordinary meanings unless the context or definition clearly indicates otherwise. Also unless expressly indicated otherwise, the use of "or" includes "and" and vice-versa. Non-limiting terms are not to be construed as limiting unless expressly stated, or the context clearly indicates, otherwise (for example, "including," "having," and "comprising" typically indicate "including without limitation"). Singular forms, including in the claims, such as "a," "an," and "the" include the plural reference unless expressly stated, or the context clearly indicates, otherwise.

The scope of the present physiologically acceptable antibiofilm compositions, systems and methods, etc., includes both means plus function and step plus function concepts. However, claims are not to be interpreted as indicating a "means plus function" relationship unless the word "means" is specifically recited in a claim, and are to be interpreted as indicating a "means plus function" relationship where the word "means" is specifically recited in a claim. Similarly, claims are not to be interpreted as indicating a "step plus function" relationship unless the word "step" is specifically recited in a claim, and are to be interpreted as indicating a "step plus function" relationship where the word "step" is specifically recited in a claim.

From the foregoing, it will be appreciated that, although specific embodiments have been discussed herein for purposes of illustration, various modifications may be made without deviating from the spirit and scope of the discussion herein. Accordingly, the systems and methods, etc., include such modifications as well as all permutations and combinations of the subject matter set forth herein and are not limited except as by the appended claims or other claim having adequate support in the discussion herein.

What is claimed is:

1. A method of inhibiting a gastrointestinal biofilm infection in a mammal, the method comprising:
    identifying the presence of the gastrointestinal biofilm infection; and
    orally administering to the mammal a therapeutically effective amount of a composition comprising:
        a multi-enzyme mixture comprising: cellulase; glucoamylase; hemicellulase/pectinase complex; beta-glucanase; an enzyme with dipeptidyl-peptidase IV (DPP-IV) activity; chitosanase; lysozyme; a *Serratia* peptidase; a chelating agent; and at least one pharmaceutically acceptable carrier,
    in an amount and for a time sufficient to cause significant biofilm degradation within the gastrointestinal system of the mammal.

2. The The method of claim 1, wherein the chelating agent is ethylenediaminetetraaceticacid (EDTA).

3. The method of claim 1, wherein the amount of cellulase per dose ranges from 1 to 10,000 CU, the amount of hemicellulase/pectinase complex ranges from 1 to 8,000 HSU, and the amount of beta-glucanase ranges from 1 to 1000 BGU.

* * * * *